United States Patent [19]

Gastrin et al.

[11] Patent Number: 5,291,897
[45] Date of Patent: Mar. 8, 1994

[54] FASTENING MEMBER

[75] Inventors: Jan M. Gastrin; Terhi Kajaste, both of Espoo, Finland

[73] Assignee: Instrumentarium Corporation, Finland

[21] Appl. No.: 755,873

[22] Filed: Sep. 6, 1991

[30] Foreign Application Priority Data

Sep. 6, 1990 [FI] Finland .................. 904407

[51] Int. Cl.⁵ .................. A61B 5/00; A61M 15/08; A62B 7/00
[52] U.S. Cl. .................. 128/716; 128/200.26; 128/207.18; 128/719; 128/911
[58] Field of Search .............. 128/716, 719, 720, 724, 128/725, 730, 746, 848, 864, 865, 200.26, 207.18, 911

[56] References Cited

U.S. PATENT DOCUMENTS

| | | | |
|---|---|---|---|
| 3,696,377 | 10/1972 | Wall | 128/716 |
| 4,167,946 | 9/1979 | Sandstrom | 128/207.17 |
| 4,344,425 | 8/1982 | Strauss | 128/864 |
| 4,420,001 | 12/1983 | Hearne | 128/724 |
| 4,777,963 | 10/1988 | McKenna | 128/724 |
| 4,903,520 | 6/1990 | Liverani | 128/746 |
| 5,056,534 | 10/1991 | Wright | 128/848 |
| 5,069,222 | 12/1991 | McDonald, Jr. | 128/724 |
| 5,074,375 | 12/1991 | Grozil | 128/864 |
| 5,105,807 | 4/1992 | Kahn et al. | 128/207.18 |

FOREIGN PATENT DOCUMENTS

| | | | |
|---|---|---|---|
| 8705798 | 10/1987 | European Pat. Off. | 128/848 |
| 2610830 | 8/1988 | France | 128/848 |
| 01391620 | 4/1988 | U.S.S.R. | 128/725 |
| 2172508 | 9/1986 | United Kingdom | 128/865 |

*Primary Examiner*—Kyle L. Howell
*Assistant Examiner*—K. M. Pfaffle
*Attorney, Agent, or Firm*—Andrus, Sceales, Starke & Sawall

[57] ABSTRACT

The invention relates to a fastening member (1) which is placed into a patient's cavity, such as a nostril, surrounded by tissue, and which allows a flow through the cavity through a port (5) and which can be joined to the measuring device via a suitable connecting piece (2). The fastening member (1) is flexible, whereby it can be formed, before being placed into the cavity, into a shape or size which fits better into the cavity, whereupon the fastening member, in the cavity, tends to return towards the original state by pressing against the surrounding wall of the cavity.

13 Claims, 4 Drawing Sheets

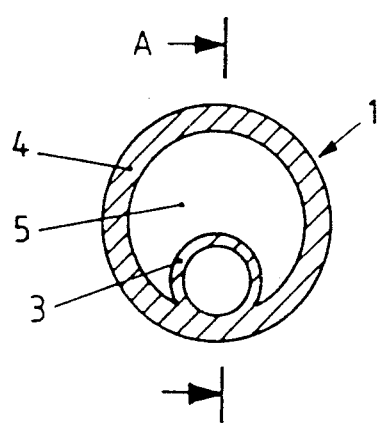
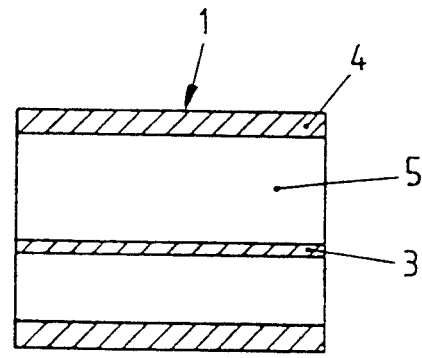
Fig 2
Fig 3
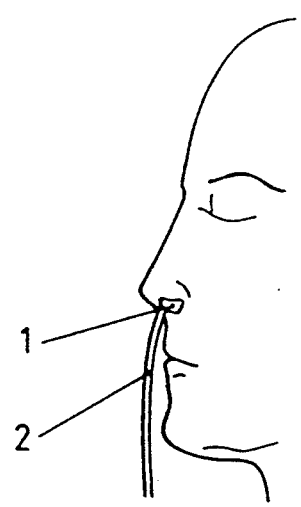
Fig 4

FASTENING MEMBER

BACKGROUND OF THE INVENTION

The invention relates to a fastening member which is placed into a patient's cavity, such as a nostril surrounded by tissue, and which allows a flow through the cavity through a port. The fastening member can be connected, by a suitable connecting piece, to a measuring device.

FIELD OF THE INVENTION

The breathing of a patient is generally controlled during anesthesia and samples are taken of the breathing, especially of a certain phase of the breathing. These samples are usually repeatedly analyzed during the operation. Thus changes in the patient's condition can be immediately observed. In order to constantly monitor breathing, the sampling tubes must be attached in one way or another to one of the respiratory passages of the patient.

DESCRIPTION OF THE PRIOR ART

Samples of the breathing are usually taken through the nostrils of the patient. There have been some problems involved, however, in attaching the sampling tube to the nostrils. According to a conventional solution, the sampling tube has been attached under the nostril with adhesive tape. The use of tape is considered to be a relatively poor solution, however, because it can irritate the skin and tends to come unstuck. When the skin is already irritated, tape cannot be used. In addition, men with beards have to be shaved if tape is to be used. The end of the sampling tube may also swing and fall into a disadvantageous position, especially in the case where it is not possible to place the tape sufficiently close to the end of the sampling tube. The sampling tube itself, which is conventionally very small in diameter and has thus taken up only a fraction of the volume of the nostril opening, has further irritated the nostrils, because the hair in the nose has been pressed only partially to the side.

The drawbacks caused by the use of tape and the thin sampling tube have been intended to be solved by developing a rigid and conical member which is pushed inside the nostril. This is thus a tube which is open on both ends thereof and its diameter increases evenly from one end of the tube to the other. A hole has been cut on the side of this conical member for pushing the end of the sampling tube inside this member in such a way that a sample is ensured from the tidal gas passing through the cone. The sampling tube is attached to the conical member either by pasting it on or by forcing the relatively rigid sampling tube through a hole made into the cone which is smaller than the sampling tube. While being pushed into the nostril the conical member is pressed against the walls of the nostril and fastened in place. The sampling tube, which projects from the side of the cone in free space, is at a relatively sharp angle to the surface of the cone, thus remains between the nostril and the cone, attempting to pry the cone in a different position, consequently irritating the patient. The conical member itself, made of inflexible material, irritates the mucous membranes even without comprising the sampling tube because it tends to form the nostril according to the configuration of the conical member. Furthermore, the above solution is relatively expensive because its manufacture requires extensive work.

The taking of respiratory samples from both the mouth and the nostrils is solved by using one member. It comprises sampling tubes extending to both nostrils which are not pressed against the nostrils, but can be freely accommodated inside the nostrils, especially without touching the surrounding tissue inside the nostril. The same member is also provided with two sampling tubes extending in front of the mouth which provide for taking samples from respiration through the mouth. A single integrated member is thus provided which is very difficult to manufacture. Furthermore, since it is disposable, its operating costs will be large. This member is attached to the skin with tape, the disadvantages of which have been described above. Similarly the irritation caused to the patient by the sampling tubes which go inside the nostrils and which are not pressed against the mucous membranes of the nostrils, have been disclosed.

SUMMARY OF THE INVENTION

The purpose of this invention is to eliminate the above problems. The purpose is thus to provide a fastening member which fits into the nostril or the ear and which is fastened to the tissue by being pressed against the wall of the cavity while the shape of the cavity remains essentially the same. The purpose is further to provide a fastening member to which it is possible to connect a sampling tube by attaching it, preferably, in the longitudinal direction of the cavity, i.e., axially. The purpose is further to achieve a fastening member which is simple to manufacture, for example from conventional materials, whereby it will be low-priced and well-adapted to making disposable products.

The characteristic features of the fastening member according to the invention are disclosed in the Claims.

The solution according to the invention is based on the fact that a fastening member is placed in a cavity in human tissue, such as a nostril, which is flexible in construction, whereby it can be pressed, before placing into a nostril, into a size or shape which fits in better. In the nostril the fastening member tends to return towards the original state while at the same time pressing against the mucous membrane of the nostril. Since the material of the fastening member is flexible, it tends to consider the shape of the nostril while expanding; the nostril is not shaped by the fastening member, but the fastening member is shaped by the nostril. Thus the fastening member must expand sufficiently in order to stick to the wall surrounding the nostril.

BRIEF DESCRIPTION OF THE DRAWINGS

In the following the invention is described in more detail by reference to the appended patent drawings, where:

FIG. 2 represents the cross section of the fastening member of FIG. 1, FIG. 3 represents the fastening member according to FIG. 2, along section A—A, FIG. 4 represents the fastening member according to FIG. 1 as taken into the nostril of the patient as the patient's face is viewed from the side.

DESCRIPTION OF THE PREFERRED EMBODIMENTS

Figure 1:
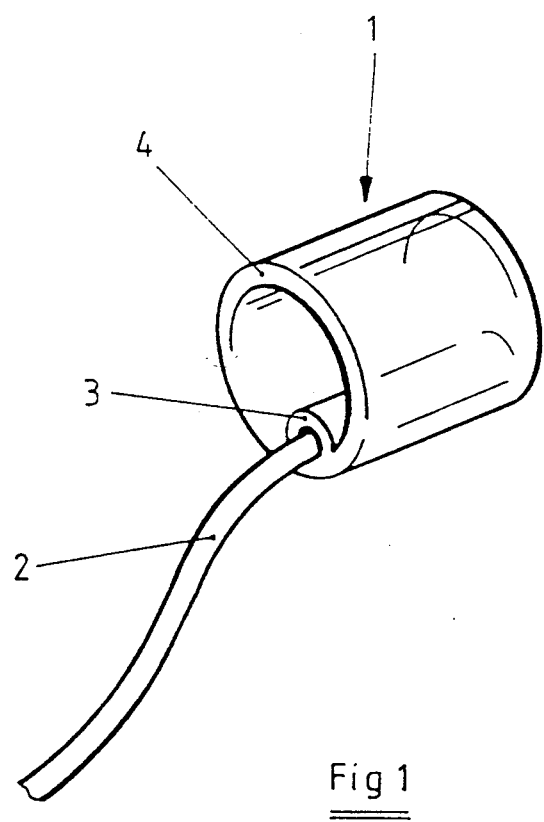
FIG. 1 represents a perspective view of the fastening member according to the invention in combination with the tube which is intended to convey samples.

FIGS. 1, 2 and 3 show fastening member 1 according to the invention which can be placed in a cavity, preferably a nostril, of a patient. This fastening member further has connecting piece 2 advantageously attached thereto which in this case is a tube along which the respiratory sample taken from the patient's nostril is conducted to the actual measuring device for analyzing, for instance, the carbon dioxide content. The said measuring device is not shown in the figure.

Inside cylindrical fastening member 1 there is, preferably, connecting member 3 for joining to connecting piece 2. The inner diameter of the connecting member is preferably so dimensioned that connecting piece 2 fits therein and remains in place under the effect of friction, whereby other fastening procedures are not necessary. Connecting piece 2 is thus joined to fastening member 1 by simply pushing it inside connecting member 3. This procedure is extremely fast and easy to perform.

FIG. 2 shows particularly port 5 which is situated inside jacket 4 of the fastening member and through which the patient is able to respirate. The port is important when samples are taken of the patient's tidal gases. If the port is blocked, the gas in the nostril does not change, whereby the sample taking is also unnecessary. In the case of FIGS. 1 to 3 the purpose of port 5 is further to provide the fastening member with flexibility.

The outer diameter of the cross section of the cylindrical fastening member 1, shown in FIGS. 1, 2 and 3, is equally large or larger than the inner diameter of the nostril in the spot where the fastening member is intended to be placed. When the form of the cross section of the fastening member deviates from the cylindrical, the diameter can be taken in any place where it is possible to attach the fastening member to the edges of the nostril. Thus the diameter in the case shown in FIG. 2, where the fastening member is circular in shape on the cross section thereof, is simply the same as the diameter of the fastening member.

The fastening member is placed into the nostril by first compressing it slightly against jacket 4 by one's fingers, for instance, and by pushing it inside the nostril. When in a suitable place, pressure on the fastening member is released, whereby it tends to return to its original shape simultaneously pressing against the mucous membranes of the nostril. The fastening member remains in this position, until it is drawn out. In FIG. 4 the fastening member is shown as pushed inside the patient's nose.

When the fastening member according to the invention is used, the walls of a cavity, such as the mucous membrane of a nostril, will not be irritated, because the shape of the wall is not intended to be essentially changed, but the shape of the fastening member changes instead. However, the diameter of the fastening member is sufficiently large for the hair of the nose which remains between the fastening member and the mucous membrane in the nostrils, for instance, to press against the mucous membrane, whereby the presence of the fastening member does not cause irritation.

The fastening member according to the invention can be advantageously manufactured by extruding a suitable grade of plastic such as silicone. In this way the fastening member with its connecting members can be manufactured in one stage of operation. When manufacturing large numbers of fastening members, a long tubular member can be made by extrusion, having a diameter similar to the one in FIG. 2, and which is then cut into pieces of a suitable length which are ready to be connected to sampling tube 2 and to be pushed thereupon into the nostril.

Figure 5:
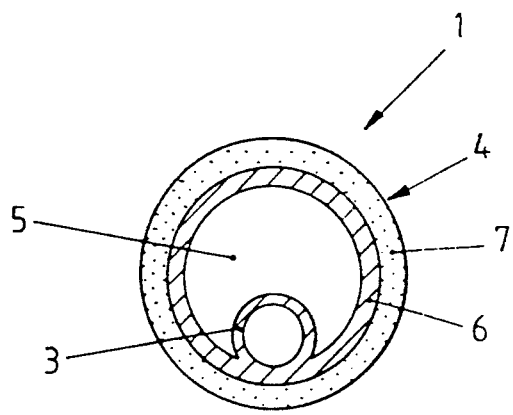
FIG. 5 represents a cross section of an alternative fastening member according to the invention.

FIG. 5 shows a cross section of another possible form of application which resembles the solution in FIG. 2. Jacket 4 consists of two layers, that is inner shell 6 and outer shell 7 surrounding it. The flexibility of the fastening member is here mainly due to outer shell 7 which contracts under pressure and expands when force is no longer acting on it. When pressing the outer shell evenly, the configuration of the fastening member does not actually change, only its size. Thus only the thickness of the outer shell changes while the inner shell remains essentially unchanged. A suitable flexible material of outer shell 7 is, for instance, cellular plastic.

Figure 6:
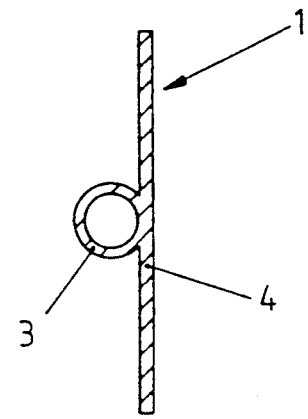
FIG. 6 represents a cross section of an alternative fastening member according to the invention.

FIG. 6 also shows an alternative form of application of the fastening member. It consists of longitudinal and vertical jacket 4 which, depending on the material used, either folds up or yields without folding when pressed and placed into the nostril.

Figure 7:
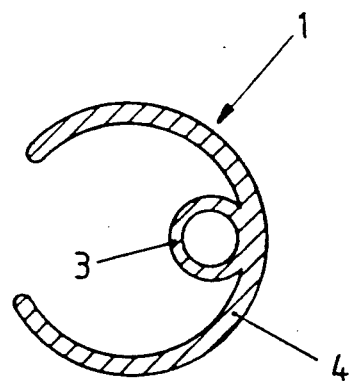
FIG. 7 represents a cross section of an alternative fastening member according to the invention.

FIG. 7 in turn gives a curved embodiment as the fastening member. By pressing on the tips of jacket 4, the member can be so formed that it fits better into the nostril.

The invention is in no way limited to the above embodiments, but different details of the invention can be varied within the Claims.

Therefore the invention is in no way limited to the shape of the fastening member. It is therefore essential from the point of view of the invention that the fastening member is flexible in construction, so that its form or size changes and tends to adapt to the walls of the cavity. Thus the fastening member could even be angular in cross section.

Figure 8:
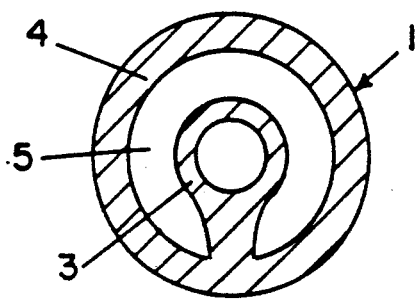
FIG. 8 represents a cross section of an alternative fastening member according to the invention.

The figures also show the practical connecting member 3. However, the invention is not restricted only to this practical solution represented in the figures but in this connection it is possible also to use several other solutions in order to join connecting piece 2 to the fastening member. The connecting member can also be situated somewhere else besides on the edge of the port. A suitable position would also be in the center of the port, as shown in FIG. 8.

Figure 9:
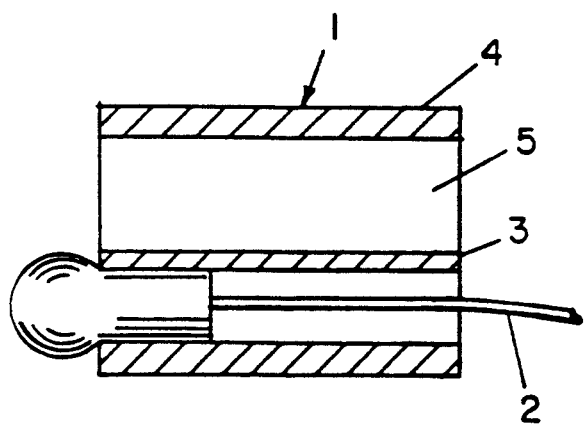
FIG. 9 represents a cross section of an alternative fastening member according to the invention.

Connecting piece 2 can also be something other than a tube leading to the measuring device. The fastening member can be provided with, for instance, a sensing element, such as a thermistor, which is adapted to detect respiration and which communicates with the actual measuring device via a conducting wire, as shown in FIG. 9.

I claim:

1. A fastening member (1) adapted to be placed in a passage of a patient for positioning a sampling means in the passage, said sampling means for conducting fluid samples to a measuring device, said passage being accessible from outside the patient's body and being lined with tissue, said fastening member comprising:

a tube formed of a deformable, resilient material, said tube having a port (5) extending therethrough parallel to a longitudinal axis of the tube, said tube being deformable by manual manipulation to facilitate placement in the passage, the resiliency of said tube tending to cause said tube to return to the undeformed state and to press against the tissue of said passage for retaining said tube in said passage, said port forming a fluid communication path through the tube to outside the patient's body for a medium in the passage when the fastening member is placed in the passage; and a connecting member (3) disposed inside said tube and attached to said tube for receiving the sampling means so that the sampling means may sample the medium in the passage.

2. A fastening member according to claim 1, wherein said connecting member extends along the inside of said tube parallel to the axis of said tube.

3. A fastening member according to claim 2, wherein said tube has an inner wall and wherein said connecting member is located on said inner wall.

4. A fastening member according to claim 1, wherein said sampling means includes an elongated connection piece, and wherein said connecting member has an opening for receiving said elongated connection piece such that said elongated connection piece extends in a direction generally parallel to the axis of said tube.

5. A fastening member according to claim 1, wherein said tube has an inner wall and wherein said connecting member is spaced from said inner wall.

6. A fastening member according to claim 1, wherein said tube has an inner wall and wherein said connecting member is located on said inner wall.

7. A fastening member according to claim 1, wherein said tube and connecting member are formed as a unitary structure.

8. A fastening member according to claim 1, wherein said tube is a cylindrical tube.

9. A fastening member according to claim 1, wherein the length of said tube is greater than its transverse dimension.

10. A fastening member according to claim 1, wherein a transverse dimension of said tube is greater than an internal dimension of the passage the point at which the fastening member is to be lodged.

11. A fastening member according to claim 1, wherein said tube contains a peripheral slit parallel to the axis of said tube to facilitate deformation of said tube.

12. A fastening member according to claim 11, wherein said tube has an inner wall, wherein said connecting member is mounted at a predetermined location on said inner wall and wherein said peripheral slit is located in said tube opposite said connecting member.

13. A fastening member according to claim 1, wherein said tube has an external jacket formed of a soft material.

* * * * *